United States Patent [19]

Dodd

[11] 4,147,625

[45] Apr. 3, 1979

[54] METHOD FOR CLARIFYING DISCOLORED TRIMETHYLHYDROQUINONE SOLUTIONS

[75] Inventor: John R. Dodd, Ponca City, Okla.

[73] Assignee: Continental Oil Company, Ponca City, Okla.

[21] Appl. No.: 900,210

[22] Filed: Apr. 26, 1978

[51] Int. Cl.$^2$ .............................................. C02B 1/20
[52] U.S. Cl. ...................................... 210/50; 210/59; 568/753
[58] Field of Search .................... 210/50, 59; 568/753

[56] References Cited

U.S. PATENT DOCUMENTS 3,981,929  9/1976  Davis et al. ........................ 568/753

FOREIGN PATENT DOCUMENTS 2250065  5/1973  Fed. Rep. of Germany ........... 568/753
1129542  1/1957  France ..................................... 568/753

Primary Examiner—Charles N. Hart
Assistant Examiner—Benoît Castel
Attorney, Agent, or Firm—Cortlan R. Schupbach, Jr.

[57] ABSTRACT

Trimethylhydroquinone (TMHQ) which is discolored in organic solution because of air oxidation can be made nearly colorless by addition of small amounts of alkali metal borohydride to the discolored solution. Products remaining in the TMHQ solution after discoloration removal can be extracted by water wash. This technique represents a very simple and efficient method for removing discoloration which has proved troublesome in the prior art.

6 Claims, No Drawings

METHOD FOR CLARIFYING DISCOLORED TRIMETHYLHYDROQUINONE SOLUTIONS

This invention relates to a method for clarifying trimethylhydroquinone in organic solutions. More specifically, this invention relates to a method for removing discoloration of trimethylhydroquinone in certain organic solvents by the addition of an effective amount of sodium borohydride.

Trimethylhydroquinone (TMHQ) is a key intermediate in the synthesis of Vitamin E ($\alpha$-tocopherol). Since Vitamin E is a product necessary for human consumption it is essential that its purity be maintained as high as possible. One of the most serious problems confronting manufacturers of Vitamin E is the discoloration of trimethylhydroquinone in air due to air oxidation which converts some trimethylhydroquinone to trimethylbenzoquinone. The result of such oxidation is solutions that are reddish-brown or orange-brown. Gas chromatographic analysis have shown such solutions to contain both trimethylbenzoquinone (TMQ) and trimethylhydroquinone (TMHQ). It has additionally been found that solutions of similar color result when pure TMQ and TMHQ are mixed together in methanol. Apparently the observed discoloration of TMHQ upon exposure to air results from partial oxidation of some of the TMHQ to TMQ which forms a colored complex with other TMHQ molecules in solution.

The prior art has recognized the problem, as can be seen in German Offenlegungschrift 2,250,065 and 2,250,066, which teach methods for obtaining clear TMHQ. These methods, however, are somewhat cumbersome as they require the addition of a hydrocarbon such as benzene or hexane to recrystallize white non-discoloring 2,3,5-trimethylhydroquinone.

However, these methods involve separation and much handling is necessary.

It would therefore be of great benefit to provide a simple and effective method for the removal of agents causing discoloration in solutions of trimethylhydroquinone.

It is therefore an object of the instant invention to provide a simple and effective method for the removal of discoloration caused by air oxidation of trimethylhydroquinone in certain organic solutions. Other objects will become apparent to those skilled in this art as the description proceeds.

It has now been surprisingly discovered that discoloration caused by the air oxidation of trimethylhydroquinone and certain organic solvents can be removed by the addition of an effective amount of an alkali metal borohydride. Boron containing coproducts resulting from this addition can be easily removed by water washing in the substantial absence of free oxygen.

Thus the instant invention provides a method for removing the discoloration caused by air oxidation of trimethylhydroquinone by the addition of alkali metal borohydride. The method is simple and convenient and is compatible with the use of trimethylhydroquinone in Vitamin E synthesis. Materials such as boric acid and/or alkali metal borates resulting from the reduction of trimethylquinone in the discolored trimethylhydroquinone are soluble in many solvents at the low levels encountered and could be removed from the crude Vitamin E in water washing steps of Vitamin E synthesis, since these materials are water soluble. The technique thus does not present any problem of contamination of Vitamin E with boron-containing compounds.

The use of nitrogen gas to exclude air from the trimethylhydroquinone/organic solution and then using the instant invention to treat any samples which have become discolored due to inadvertant air contamination enable trimethylhydroquinone to be handled and used effectively and efficiently in carrying out various reactions. As set forth above, it is important that trimethylhydroquinone be purified prior to use in Vitamin E synthesis, since trimethylbenzoquinone present would likely remain unchanged during the Vitamin E synthesis and contaminate the Vitamin E itself.

The instant invention is more concretely described with reference to the examples below wherein all parts and percentages are by weight unless specified. The examples are provided to illustrate the instant invention and not to limit it.

In the examples below trimethylhydroquinone was investigated in its discolored state in various organic solvents, then applying the method of the instant invention.

EXAMPLE 1

A feed consisting of 21.92 grams of trimethylbenzoquinone (TMQ) and 87.7 grams of methanol was hydrogenated in a continuous hydrogenation reactor at 60° C. and 50 pounds per square inch gauge (psig) with a liquid hourly space velocity (LHSV) of 0.72. The hydrogenated product stream, which was collected under a hydrogen atmosphere, was colorless. A portion of the hydrogenated reaction mixture was exposed to air and within a few minutes discolored to a reddish brown solution. The addition of a few grains of sodium borohydride to the discolored solution caused it to become colorless within a few minutes.

EXAMPLE 2

A discolored orange brown trimethylhydroquinone (TMHQ) solution was made by dissolving 0.2 grams of slightly discolored TMHQ in 0.8 grams of dimethylformamide (DMF). Gas chromatographic analysis of the solution indicated that TMQ was present at a level of 2.07 weight percent, (20.9 mg of TMQ). Sodium borohydride (1 mg) was added and the mixture was shaken for 4 minutes at the end of which time the solution remained colored. After four additional minutes had elapsed, an additional 1.9 mg of sodium borohydride was added. After frequent shaking for nine minutes most of the discoloration had disappeared. A pale peach colored solution remained. After an additional six minutes the solution was nearly colorless. Excess sodium borohydride was still present at this time.

EXAMPLE 3

A discolored red brown TMHQ solution was made by dissolving 1 gram of slightly discolored TMHQ in four grams of methanol. Gas chromatographic analysis of this solution indicated that TMQ was present at a level of 0.49 weight percent (solution contained 24.4 mg of TMQ). 2 mg of sodium borohydride was added and after four minutes the solution was a much lighter orange pink than the original red brown solution. After an additional three minutes, 2.2 mg of additional sodium borohydride was added. The solution became essentially colorless within one minute of the second addition.

EXAMPLE 4

An orange gold discolored TMHQ solution was made by dissolving 1 gram of slightly discolored TMHQ in 4 grams of tetrahydrofuran (THF). Gas chromatographic analysis of this solution indicated that the TMQ was present at a level of 0.34 weight percent (the solution contained 17 mg of TMQ). One mg of sodium borohydride was added and the mixture shaken for nine minutes. No change in the level of discoloration was observed. An additional 2 mg of sodium borohydride was added and the mixture shaken occasionally over a 45 minute period. At the end of this time the sample appeared to have the same level of discoloration as initially observed. The sample was allowed to stand for approximately 68 hours after which time the sample had become much lighter and was a pale straw colored solution.

EXAMPLE 5

Qualitative tests were made regarding the use of sodium borohydride to discolor TMHQ solutions using several solvents. In each case 200 mg of slightly discolored TMHQ was dissolved in 0.8 to 2.4 grams of a given solvent and then approximately 2 to 6 mg of additional TMQ was added to give more intense discoloration. Small amounts ranging from 2 to 6 mg of sodium borohydride were added and the samples were shaken frequently as they were being observed. Additional small portions of sodium borohyride were added at intervals of approximately 10 minutes. The solvents studied were diethyl ether, acetone, ethanol, acetic acid, and ethyl acetate. Sodium borohydride reacted vigorously with acetic acid with liberation of hydrogen and no removal of discoloration was observed to occur in this solvent. When ethanol was used as a solvent the discoloration was completely removed yielding a clear solution. When ethyl acetate was used the discoloration was removed very slowly and removal was incomplete. The other solvents studied appeared to be ineffective for removal of discoloration in TMHQ solutions. In the case of acetone a dark solid was observed to form at the liquid sodium borohydride solid interface and the level of discoloration in the solution did not decrease.

EXAMPLE 6

An orange brown discolorated TMHQ solution was made by dissolving 1 gram of TMHQ already slightly discolored in 9.01 grams of acetonitrile. Gas chromatographic analysis of the solution indicated that TMQ was present at a level of 0.74 weight percent (solution contained 74.2 mg of TMQ). Sodium borohydride at a level of 4.7 mg was added. After two minutes the solution was much lighter and had a pinkish coloration. After four minutes with frequent shaking the solution was essentially colorless and had a slight milky appearance. A small amount of sodium borohydride was still present at the bottom of this sample after it had become colorless.

EXAMPLE 7

A discolored (orange-brown) solution of TMHQ in dimethylsulfoxide was prepared using approximately 0.1 g of slightly discolored TMHQ and approximately 0.6 g of dimethylsulfoxide. Approximately 6 mg of sodium borohydride was added and the mixture was shaken at frequent intervals for 5 minutes. A lighter orange-brown color resulted. Another portion (~6 mg) of sodium borohydride was added. After an additional 4 minutes with frequent shaking, the color was a pale yellow-brown. After 3 additional minutes, the solution was only faintly yellow and essentially colorless. Excess sodium borohydride remained undissolved at this time.

EXAMPLE 8

A dilute but saturated solution of TMHQ (slightly discolored) and n-pentanol was prepared (~2 g). Approximately 6 mg of sodium borohydride was added to the orange-brown solution and the mixture was shaken for a few minutes. Another portion (~6 mg) of sodium borohydride was added and the mixture was shaken frequently for 9 minutes. At this time the TMHQ solution was faintly yellow and essentially colorless and excess sodium borohydride remained undissolved.

Thus from the experiments carried out beforehand it has been discovered that the affect of the instant invention depends in a large extent on whether the solvent is an effective solvent for both TMHQ and alkali metal borohydrides and has no undesirable side reactions. In any case a simple experiment would enable one skilled in the art to determine whether such solvents were effective with the alkali metal borohydride. Some solvents are not suitable for the process of the instant invention. Representative examples of such solvents are ether, acetone, toluene acetic acid and other acids which would react with the alkali metal borohydride.

Some solvents are marginal in effect such that the removal of the discoloration occur slowly and may not be complete. Examples of such solvents are ethyl acetate and tetrahydrofuran (THF).

Preferred solvents are those which solubilize both TMHQ and alkali metal borohydrides and are suitable for essentially complete removal of discoloration. Representative examples of such solvents include alcohols containing from 1 to 5 carbon atoms (such as methanol, ethanol and pentanol), sulfoxides, such as dimethylsulfoxide, amides such as N,N'Dimethylformamide and N-methyl-2-pyrrolidone and nitriles such as acetonitrile as well as other solvents which meet solubility requirements, such as hexamethyl phosphoric triamide. As stated above a simple experimentation with the solvent of choice will reveal the effectiveness of the instant invention.

Although the exact reason for the removal of the discoloration is not completely established, a hypothesis has been formulated. The hypothesis is presented merely for purposes of explanation and the instant invention is not bound or limited by the hypothesis. The discoloration of TMHQ observed in the instant invention is believed due to the air oxidation of TMHQ to TMQ in solution. The resulting TMQ forms a complex with TMHQ known as a quinhydrone having the approximate structure:

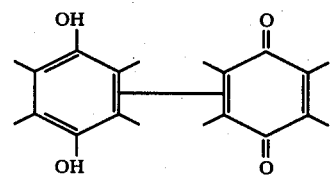

Quinhydrone complexes strongly absorb visible light and would appear very dark i.e. black or nearly so under neat (no solvent) conditions. Thus, even though TMHQ is a white solid and TMQ is a low melting yellow solid the quinhydrone resulting from a combination of the two would be very dark even in low concentrations of TMHQ. The combination of TMQ and TMHQ in most solvents would likely form weak quinhydrone complexes bonded by weak molecular intermolecular forces, which complexes would appear red brown or orange brown in very dilute solution. Apparently the presence of the quinhydrone complexes are responsible for the observed discoloration in oxidized TMHQ solutions.

The treatment of such discolored TMHQ solutions in effective solvents with small amounts of the alkali metal borohydrides of the instant invention results in the disappearance of the discoloration and the simultaneous disappearance of TMQ from the solution. Apparently the sodium borohydride is reducing the TMQ, either while present in the quinhydrone complex, or as the free quinone in equilibrium with the quinhydrone complex. Reduction of the TMQ would remove the colored weak quinhydrone complex from the system and result in a much lighter or nearly colorless solution. The hypothecated reduction reaction is set forth below.

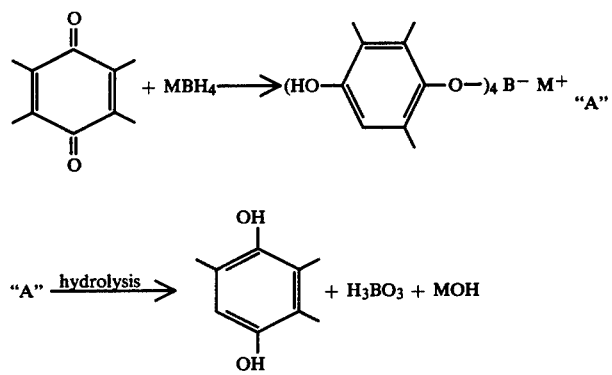

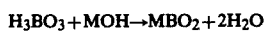

wherein M is an alkali metal. In a basic solution borate salts may result as set forth below because of the neutralization reaction.

$$H_3BO_3 + MOH \rightarrow MBO_2 + 2H_2O$$

Using this hypothesis, one mole of alkali metal borohydride can reduce four moles of quinone. Competing reactions such as hydrolysis of the alkali metal borohydride can occur, resulting in a somewhat greater amount of alkali metal borohydride being required than the theoretical 1–4 ratio. Experimentally, it has been found that sodium borohydride levels of from 1 to about 3 times the theoretical amount are sufficient to remove the discoloration in effective solvents. This amount corresponds to approximately 0.063 to about 0.189 parts by weight of alkali metal borohydride per part by weight of TMQ in the discolored solution.

Representative examples of alkali metal borohydrides effective in the process of the instant invention are lithium borohydride, potassium borohydride, sodium borohydride, or mixtures of these.

With specific reference to the synthesis of Vitamin E, TMHQ is normally condensed with phytol alcohol or isophytol alcohol in approximately a 1:1 molar ratio in the presence of an acid catalyst such as zinc chloride. The reaction is often carried out in toluene with azeotropic removal of water formed in the reaction. The general reaction scheme is set forth below.

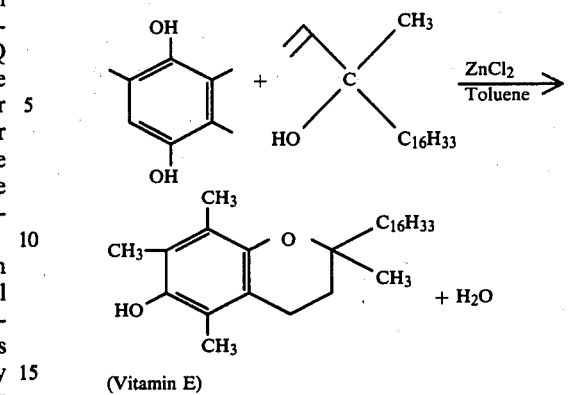

(Vitamin E)

Thus when TMHQ which had been discolored and clarified with an alkali metal borohydride was used in the synthesis described above, the waterwash step would be used to hydrolyze the aryl borate intermediate. Acid or base may have to be added to affect hydrolysis under conditions which would not be detrimental toward the formation of α-tocopherol. The resulting boric acid or borate salts which are formed are water soluble and can be removed from the Vitamin E in the waterwash step.

Thus it is apparent that a simple and effective method has been found for the removal of discoloration from trimethylhydroquinone in certain organic solvents. The method is easily carried out and suitable solvents may be determined with a simple one step test.

While certain embodiments and details have been shown for the purpose of illustrating this invention, it will be apparent to those skilled in this art that various changes and modifications may be made herein without departing from the spirit or the scope of the invention.

I claim:

1. A method for removing discoloration in trimethylhydroquinone dissolved in effective organic solvents, said discoloration caused by air oxidation, the method comprising adding effective amounts of alkali metal borohydrides selected from the group consisting of lithium borohydride, potassium borohydride, sodium borohydride, or mixtures of these to the discolored solution.

2. A method as described in claim 1 wherein the boron containing coproducts resulting from the addition of alkali metal borohydrides are removed by water washing in the substantial absence of free oxygen.

3. A method as described in claim 2 wherein the clarification is carried out in a polar solvent capable of solubilizing trimethylhydroquinone and alkali metal borohydrides.

4. A method as described in claim 2 wherein the organic solution is selected from the group consisting of methanol, pentanol, ethanol, N,N-dimethylformamide, acetonitrile, dimethylsulfoxide, ethyl acetate, tetrahydrofuran and hexamethyl phosphoric triamide.

5. A method as described in claim 2 wherein the borohydride compound is added to the discolored solution in a weight ratio of from about 0.063 to about 0.189 parts of borohydride to parts of quinone present.

6. A method as described in claim 2 wherein the process is carried out during the synthesis of Vitamin E.

* * * * *